(12) United States Patent
Navot et al.

(10) Patent No.: US 10,387,723 B2
(45) Date of Patent: Aug. 20, 2019

(54) SYSTEM AND METHOD OF UNIQUE IDENTIFYING A GEMSTONE

(71) Applicant: Sarine Color Technologies Ltd., Hod HaSharon (IL)

(72) Inventors: Yifta Navot, Moledet (IL); Omri Spirman, Even Yehuda (IL); Ofek Shilon, Kfar Saba (IL); Abraham Kerner, Herzliya (IL); Uzi Levami, Hod Hasharon (IL)

(73) Assignee: Sarine Color Technologies Ltd., Hod HaSharon (IL)

( * ) Notice: Subject to any disclaimer, the term of this patent is extended or adjusted under 35 U.S.C. 154(b) by 44 days.

(21) Appl. No.: 15/564,565

(22) PCT Filed: May 18, 2016

(86) PCT No.: PCT/IL2016/050524
§ 371 (c)(1),
(2) Date: Oct. 5, 2017

(87) PCT Pub. No.: WO2016/185472
PCT Pub. Date: Nov. 24, 2016

(65) Prior Publication Data
US 2018/0082116 A1 Mar. 22, 2018

Related U.S. Application Data
(60) Provisional application No. 62/164,994, filed on May 21, 2015.

(51) Int. Cl.
*G06K 9/00* (2006.01)
*G01N 21/87* (2006.01)
*G06K 9/62* (2006.01)

(52) U.S. Cl.
CPC ......... *G06K 9/00577* (2013.01); *G01N 21/87* (2013.01); *G06K 9/6202* (2013.01); *G06K 9/627* (2013.01); *G06K 9/629* (2013.01)

(58) Field of Classification Search
CPC ........ G01N 21/47; G01N 21/41; G01N 21/87; G01N 21/8806; G01N 21/00; G01N 21/01;
(Continued)

(56) References Cited

U.S. PATENT DOCUMENTS

| 1,744,485 A | 1/1930 | Riedl et al. |
| 3,740,142 A | 6/1973 | Takubo |

(Continued)

FOREIGN PATENT DOCUMENTS

| CA | 2162532 | 5/1997 |
| CA | 2162532 A1 | 5/1997 |

(Continued)

OTHER PUBLICATIONS

International Search Report and Written Opinion received in PCT/IL2016/050524 dated Aug. 8, 2016.
(Continued)

*Primary Examiner* — Aklilu K Woldemariam
(74) *Attorney, Agent, or Firm* — ISUS Intellectual Property PLL; A. Jason Mirabito

(57) ABSTRACT

There is provided a computerized system and method of generating a unique identification associated with a gemstone, usable for unique identification of the gemstone. The method comprises: obtaining one or more images of the gemstone, the one or more images captured at one or more viewing angles relative to the gemstone and to a light pattern, thus giving rise to a representative group of images; processing the representative group of images to generate a set of rotation-invariant values informative of rotational (Continued)

cross-correlation relationship characterizing the images in the representative group; and using the generated set of rotation-invariant values to generate a unique identification associated with the gemstone. The unique identification associated with the gemstone can be further compared with an independently generated unique identification associated with the gemstone in question, or with a class-indicative unique identification.

11 Claims, 11 Drawing Sheets

(58) Field of Classification Search
CPC ............. G01N 2223/05; G01N 33/381; G06K 9/00577; G06K 9/3233; G06K 9/6202; G06K 9/627; G06K 9/629; G06K 9/4652; G06K 9/4661; B01J 19/081; B23K 2101/007; B41J 2/1404; G09B 23/22; G09B 23/26; G09B 23/40; G09B 25/00; G09B 5/02; G01J 3/463; G01J 5/08; G01J 4/00; G06Q 30/0278; G06Q 30/0601; G06Q 30/0621; G06Q 30/0613; G06Q 30/0603; G06Q 10/1095; G06Q 30/0631; G06F 17/50; B33Y 80/00; H04N 7/18
USPC ....... 382/100, 115, 141, 181, 125, 128, 209; 356/30, 448, 445, 418, 419
See application file for complete search history.

(56) References Cited

U.S. PATENT DOCUMENTS

| | | | |
|---|---|---|---|
| 3,947,120 A | 3/1976 | Bar-Issac et al. | |
| 4,012,141 A | 3/1977 | Hanneman | |
| 4,125,770 A | 11/1978 | Lang et al. | |
| 4,200,506 A | 4/1980 | Dreschhoff et al. | |
| 4,316,385 A | 2/1982 | DeVries et al. | |
| 4,467,172 A | 8/1984 | Ehrenwald et al. | |
| 4,799,786 A | 1/1989 | Gerrard | |
| 5,673,338 A | 9/1997 | Denenberg et al. | |
| 6,975,755 B1 * | 12/2005 | Baumberg | G06K 9/4642 345/419 |
| 8,317,521 B2 * | 11/2012 | Lapa | G09B 5/02 356/30 |
| 2004/0072137 A1 * | 4/2004 | Lapa | G09B 5/02 434/386 |
| 2005/0036132 A1 | 2/2005 | Lapa et al. | |
| 2005/0190356 A1 * | 9/2005 | Sasian | G01N 21/87 356/30 |
| 2006/0196858 A1 * | 9/2006 | Barron | A44C 17/00 219/121.69 |
| 2009/0234754 A1 * | 9/2009 | Lapa | G06Q 30/0278 705/26.1 |
| 2010/0092067 A1 * | 4/2010 | Ellawand | G01N 21/41 382/141 |
| 2011/0310246 A1 * | 12/2011 | Hornabrook | G01N 21/87 348/142 |
| 2012/0007971 A1 * | 1/2012 | Schnitzer | G01N 21/87 348/61 |
| 2014/0063485 A1 * | 3/2014 | Palmieri | G01N 21/87 356/30 |
| 2014/0104595 A1 | 4/2014 | Ninomiya et al. | |
| 2015/0377793 A1 * | 12/2015 | Levami | G01N 21/87 702/81 |
| 2016/0004926 A1 * | 1/2016 | Kerner | G01B 11/24 348/46 |
| 2016/0232432 A1 * | 8/2016 | Regev | G02B 21/0028 |
| 2017/0343493 A1 * | 11/2017 | Reischig | G01N 23/20 |

FOREIGN PATENT DOCUMENTS

| | | |
|---|---|---|
| GB | 1416568 | 12/1975 |
| GB | 1416568 A | 12/1975 |
| GB | 2121535 A | 12/1983 |
| IL | 64274 | 3/1986 |
| IL | 64274 A | 3/1986 |
| JP | 2003042964 A | 2/2003 |
| JP | 2006145280 A | 6/2006 |
| WO | 2010/103526 | 9/2010 |
| WO | 2013/006677 | 1/2013 |
| WO | 2013006677 A1 | 1/2013 |
| WO | 2016030833 | 3/2016 |

OTHER PUBLICATIONS

International Search Report and Written Opinion for International Application No. PCT/IL2016/050524 dated Aug. 9, 2016.

* cited by examiner

SYSTEM AND METHOD OF UNIQUE IDENTIFYING A GEMSTONE

TECHNICAL FIELD

The presently disclosed subject matter relates, in general, to the field of gemstone identification.

BACKGROUND

Gemstones are commonly classified according to various properties, including weight, color and clarity, properties which greatly affect the value of the gemstone. An expert gemologist is usually required to evaluate these properties in order to determine the value of the gemstone and also to identify and distinguish one particular gemstone from all other gemstones. A need therefore exists for a method and apparatus to identify gemstones, enabling even a non-expert to quickly and positively identify any particular gemstone and to distinguish it from others.

A number of methods have been proposed in the past for identifying gemstones, particularly diamonds. Among these known methods are those based on: reflection techniques, as illustrated in U.S. Pat. Nos. 3,740,142 and 3,947,120; geometric scattering techniques, as illustrated in U.S. Pat. No. 4,012,141; Raman refraction techniques, as illustrated in U.S. Pat. No. 4,799,786; ion implantation techniques, as illustrated in U.S. Pat. Nos. 4,200,506 and 4,316,385; laser micro-engraving techniques, as illustrated in U.S. Pat. No. 4,467,172 and Israel Patent No. 64274; and x-ray techniques, as illustrated in U.S. Pat. No. 4,125,770. However, none of these known techniques has yet found widespread use, primarily because of one or more of the following drawbacks: the high cost and cumbersome procedures required for identifying the diamonds; the lack of reproducibility enabling the same identification results to be obtained using various types of identification apparatus and working conditions; and/or the inability of identifying the diamond while held in a setting.

GENERAL DESCRIPTION

In accordance with certain aspects of the presently disclosed subject matter, there is provided a computerized method of generating a unique identification associated with a gemstone and usable for unique identification of the gemstone. The method comprises: obtaining one or more images of the gemstone, the one or more images captured at one or more viewing angles relative to the gemstone and to a light pattern, thus giving rise to a representative group of images; processing the representative group of images to generate a set of rotation-invariant values informative of rotational cross-correlation relationship characterizing the images in the representative group; and using the generated set of rotation-invariant values to generate a unique identification associated with the gemstone. The rotation-invariant values can be informative of rotational cross-correlation relationship in spatial domain or frequency domain. The generated unique identification can be further stored in association with the gemstone.

In accordance with further aspects of the presently disclosed subject matter, processing the representative group of images comprises generating a composite image corresponding to the images in the representative group and calculating the set of rotation-invariant values based on cross-correlation relationship between the composite image and rotation versions thereof. Optionally, the rotation versions are evenly spaced within a predetermined range.

Optionally, the composite image can be generated using one of the following: weighted average of pixel values over the one or more images in the representative group; weighted average of pixel values over the one or more post-processed derivatives of images in the representative group; un-weighted average of pixel values over the one or more images in the representative group; un-weighted average of pixel values over the one or more post-processed derivatives of images in the representative group.

Optionally, the processing can comprise determining within the composite image a gemstone image area and providing the further processing merely with respect to the pixels within the gemstone image area. Alternatively or additionally, the processing can comprise: dividing the composite image into a plurality of concentric areas; for each given area, generating a per-area set of rotation-invariant values informative of rotational cross-correlation relationship between a given area and its rotation versions; and generating unique identification corresponding to all per-area sets of rotation-invariant values respectively generated, respectively, to each of the concentric areas.

In accordance with further aspects of the presently disclosed subject matter, the method can further comprise: comparing the unique identification associated with the gemstone with an independently generated unique identification associated with a gemstone in question; and identifying the gemstone in question as being the same gemstone when the independently generated unique identification matches the unique identification, wherein the unique identification and the independently generated unique identification are generated by the equivalent techniques enabling compatibility of the unique identifications.

In accordance with further aspects of the presently disclosed subject matter, the method can further comprise: comparing the unique identification associated with the gemstone with a class-indicative unique identification associated with a given class of gemstones; and identifying the gemstone as belonging to the given class of gemstones when the unique identification matches the class-indicative unique identification, wherein the unique identification and the class-indicative unique identification are generated by the equivalent techniques enabling compatibility of the unique identifications. The class-indicative unique identification can correspond to a unique identification of a reference gemstone representing the given class or can be generated using statistical data resulting from processing representative groups of images obtained for a statistically reliable amount of gemstones corresponding to the given class.

In accordance with other aspects of the presently disclosed subject matter and, optionally, in combination with any of the appropriate above aspects, there is provided a computerized method of uniquely identifying a gemstone, the method comprising: obtaining a first unique identification associated with a first gemstone, the first unique identification corresponding to a first set of rotation-invariant values informative of rotational cross-correlation relationship characterizing a first representative group of one or more first images of the first gemstone, the one or more first images captured at one or more viewing angles relative to the first gemstone and to a first light pattern; obtaining a second unique identification associated with a second gemstone, the second unique identification corresponding to a second set of rotation-invariant values informative of rotational cross-correlation relationship characterizing a second representative group of one or more second images of the second gemstone, the one or more second images captured at one or more viewing angles relative to the second gemstone and to a second light pattern independently from capturing the one or more first images; calculating a matching score for said first and second unique identifications, the matching score being informative of a match between said first and second unique identifications; and identifying the first gemstone associated with the first unique identification and the second gemstone associated with the second unique identification as being the same gemstone when the matching score meets a predefined matching criterion.

In accordance with further aspects of the presently disclosed subject matter and, optionally, in combination with any of the appropriate above aspects, obtaining the first unique identification can comprise generating a first composite image corresponding to the images in the first representative group and calculating the first set of rotation-invariant values based on cross-correlation relationship between the first composite image and rotation versions thereof; obtaining the second unique identification can comprise generating a second composite image corresponding to the images in the second representative group and calculating the second set of rotation-invariant values based on cross-correlation relationship between the second composite image and rotation versions thereof; wherein the first set is compatible with the second set.

In accordance with further aspects of the presently disclosed subject matter and, optionally, in combination with any of the appropriate above aspects, the method can further comprise: dividing the first composite image into a plurality of first concentric areas and obtaining the first unique identification informative of all sets of rotation-invariant values generated, respectively for each first concentric area; dividing the second composite image into a plurality of second concentric areas corresponding to the first concentric areas and obtaining the second unique identification informative of all sets of rotation-invariant values generated, respectively for each second concentric area; and wherein calculating the matching score comprises separately calculating matching scores for each pair of a first concentric area and a corresponding second concentric area. Optionally, the first gemstone associated with the first unique identification and the second gemstone associated with the second unique identification can be identified as being the same gemstone when matching scores of each pair meet respective predefined matching criterion. Optionally, matching criterion can differ for different pairs.

In accordance with further aspects of the presently disclosed subject matter and, optionally, in combination with any of the appropriate above aspects, the one or more first images can be captured by a first machine and the one or more second images can be captured by a second machine other than the first machine, each machine calibrated with respect to the environment.

In accordance with other aspects of the presently disclosed subject matter, there is provided a computerized system capable of generating a unique identification associated with a gemstone, the system comprising a processor configured to operate in accordance with any appropriate combination of the above aspects.

In accordance with other aspects of the presently disclosed subject matter and, optionally, in combination with any of the appropriate above aspects, there is provided a computerized system comprising a processor configured to: obtain a first unique identification associated with a first gemstone, the first unique identification corresponding to a first set of rotation-invariant values informative of rotational cross-correlation relationship characterizing a first representative group of one or more first images of the first gemstone, the one or more first images captured at one or more viewing angles relative to the first gemstone and to a first light pattern; obtain a second unique identification associated with a second gemstone, the second unique identification corresponding to a second set of rotation-invariant values informative of rotational cross-correlation relationship characterizing a second representative group of one or more second images of the second gemstone, the one or more second images captured at one or more viewing angles relative to the second gemstone and to a second light pattern independently from capturing the one or more first images; calculate a matching score for said first and second unique identifications, the matching score being informative of a match between said first and second unique identifications; and identify the first gemstone associated with the first unique identification and the second gemstone associated with the second unique identification as being the same gemstone when the matching score meets a predefined matching criterion.

Optionally, the system can be configured to generate the first and/or the second unique identifications. Alternatively or additionally, the system can be configured to receive the first and/or the second unique identifications from external source(s) configured to generate and/or to store the first and/or the second unique identifications.

In accordance with other aspects of the presently disclosed subject matter and, optionally, in combination with any of the appropriate above aspects, there is provided a computerized system comprising a processor configured to: obtain a first unique identification associated with a gemstone, the unique identification corresponding to a set of rotation-invariant values informative of rotational cross-correlation relationship characterizing a representative group of one or more images of the gemstone, the one or more images captured at one or more viewing angles relative to the first gemstone and to a first light pattern; obtain a class-indicative unique identification associated with a given class of gemstones; calculate a matching score for the unique identification associated with the gemstone and the class-indicative unique identification, the matching score being informative of a match between said unique identifications; and identify the gemstone as belonging to the given class of gemstones when the unique identification matches the class-indicative unique identification, wherein the unique identification and the class-indicative unique identification are generated by the equivalent techniques enabling compatibility of the unique identifications.

Optionally, the system can be configured to generate the unique identification associated with the gemstone and/or the class-indicative unique identification. Alternatively or additionally, the system can be configured to receive the unique identification associated with the gemstone and/or the class-indicative unique identification from an external source configured to generate and/or to store the unique identification associated with the gemstone and/or the class-indicative unique identification.

BRIEF DESCRIPTION OF THE DRAWINGS

In order to understand the presently disclosed subject matter and to see how it can be carried out in practice, the subject matter will now be described, by way of non-limiting example only, with reference to the accompanying drawings, in which:

FIGS. 4b-4e illustrate exemplified composite images generated for representative group of four images illustrated in FIG. 4a;

DETAILED DESCRIPTION

Figure 1A:
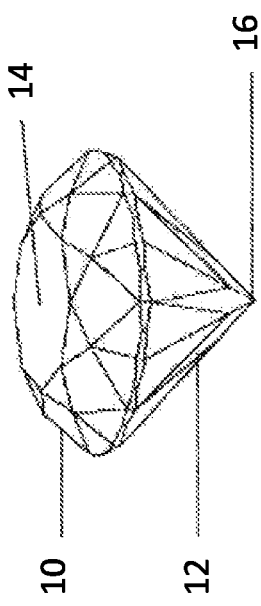
FIGS. 1a and 1b illustrate an exemplified standard round brilliant cut diamond from an elevated side-on perspective and from a top-down view respectively.

In the following detailed description, numerous specific details are set forth in order to provide a thorough understanding of the disclosed subject matter. However, it will be understood by those skilled in the art that the present disclosed subject matter can be practiced without these specific details. In other instances, well-known methods, procedures, and components have not been described in detail so as not to obscure the present disclosed subject matter.

In the drawings and descriptions set forth, identical reference numerals indicate those components that are common to different embodiments or configurations.

Unless specifically stated otherwise, as apparent from the following discussions, it is appreciated that throughout the specification discussions utilizing terms such as "generating", "obtaining", "determining", "processing", "calculating", "combining", "selecting", "dividing", or the like, include action and/or processes of a computer that manipulate and/or transform data into other data, said data representing physical quantities, e.g. such as electronic quantities, and/or said data representing the physical objects. The term "computer" should be expansively construed to cover any kind of hardware-based electronic device with data processing capabilities, including, by way of non-limiting examples, the computerized system, and the processor or processing unit disclosed in the present application. The terms "computer", "processor", and/or "processing unit" can include a single computer/processor/processing unit or a plurality of distributed or remote such units.

The operations in accordance with the teachings herein can be performed by a computer specially constructed for the desired purposes or by a general purpose computer specially configured for the desired purpose by a computer program stored in a non-transitory computer readable storage medium. The present disclosure can also encompass the computer program for performing the method of the invention.

The term "non-transitory" is used herein to exclude transitory, propagating signals, but to otherwise include any volatile or non-volatile computer memory technology suitable to the presently disclosed subject matter.

The term "criterion" used in this patent specification should be expansively construed to include any compound criterion, including, for example, several criteria and/or their logical combinations.

It is appreciated that, unless specifically stated otherwise, certain features of the presently disclosed subject matter, which are described in the context of separate embodiments, can also be provided in combination in a single embodiment. Conversely, various features of the presently disclosed subject matter, which are described in the context of a single embodiment, can also be provided separately or in any suitable sub-combination.

For purpose of illustration only, some embodiments of the following description are provided with respect to diamonds. Embodiments are, likewise, applicable to other kinds of gemstones that have suitable optical behaviors to be scanned in the apparatus as described below, such as, e.g., gemstones that are relatively transparent and for which the light can be internally reflected.

Figure 1B:
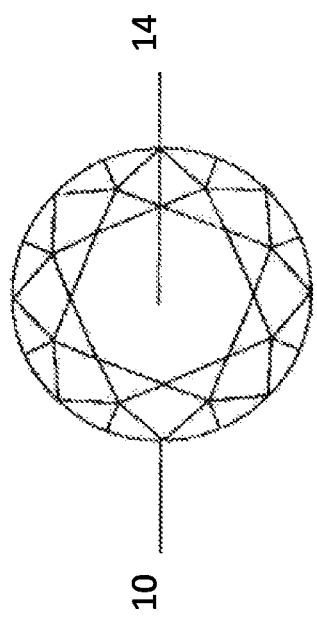

Bearing this in mind, attention is now drawn to FIGS. 1a and 1b, schematically illustrating an exemplified standard round brilliant cut (RBC) diamond from an elevated side-on perspective and from a top-down view respectively.

FIG. 1a shows the diamond from an elevated side-on view. The top most domed-shaped portion of the diamond is known as the crown 10. The bottom most conical portion of the diamond is known as the pavilion 12. At the top of crown 10 at the centre is a relatively large facet known as the table 14. The bottom most point of the pavilion 12 is known as the culet 16. FIG. 1b shows the RBC diamond from a top-down view, looking along an axis from the centre of the table 14 through the culet 16. There are 32 facets on the crown 10 of the RBC diamond, not including table 14, and 24 facets on the pavilion, not including culet 16. It can be seen that the radial facets of the RBC diamond (56 in total plus one for the table and one for the culet) have an 8-fold symmetry about an axis passing though the centre of table 14 and culet 16.

Figure 2:
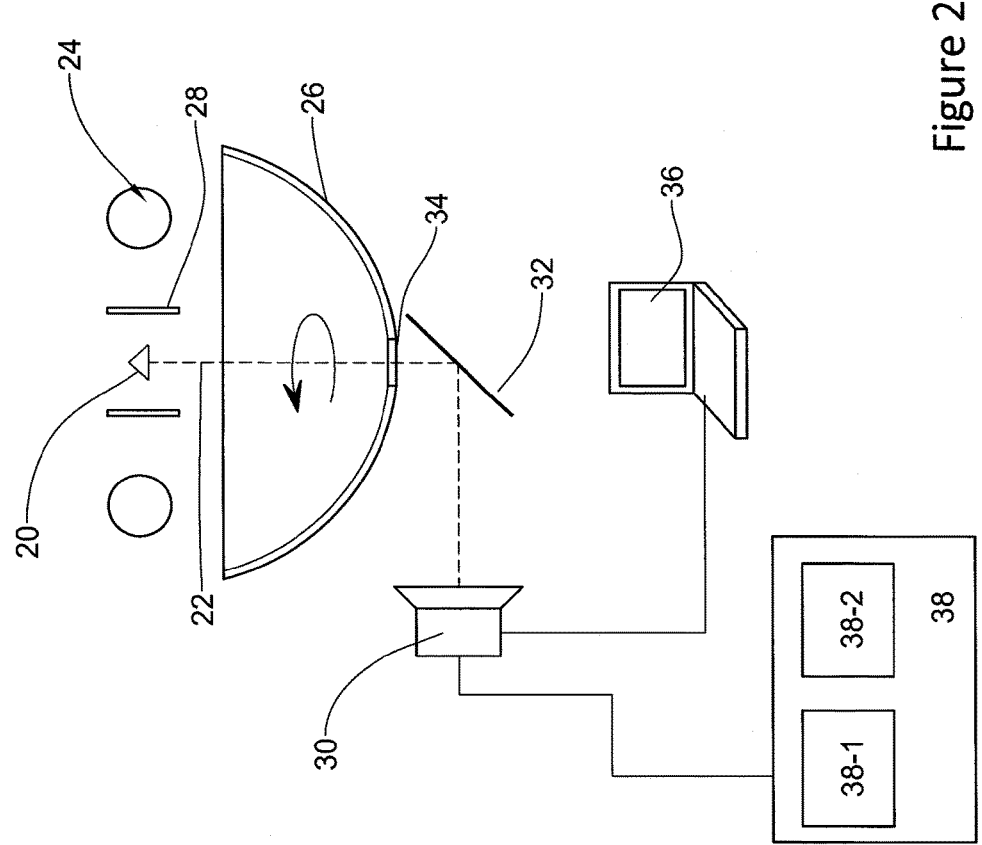
FIG. 2 schematically illustrates an apparatus capable of generating data usable for determining a fingerprinting of a gemstone in accordance with certain embodiments of the presently disclosed subject matter.

Reference is now made to FIG. 2, schematically illustrating an apparatus capable of scanning the gemstone and generating image data usable for determining a unique identification of a gemstone in accordance with certain embodiments of the presently disclosed subject matter. A gemstone 20 (e.g. a cut diamond) is placed on a platform (not shown) at an observation position with its table-side face-down. The platform is an optically clear glass plane of regular thickness arranged within the apparatus so that it is substantially horizontal when the apparatus is in a horizontal position. The platform can be coated with an anti-reflection coating and provided with a small ring underneath to reduce glare. The apparatus is mounted in a housing (not shown) which prevents external light from reaching the diamond 20 and dust from entering the mechanical and optical components. The housing has an access lid above the platform for placing and removing a gemstone to be measured. The inner surface of the housing and lid above the region of the platform is coated with an unreflective material so that substantially no light is reflected back from the lid or housing towards the gemstone or platform.

According to certain embodiments, diamond 20 can be illuminated by an annular light 24, such as, e.g., a fluorescent tube light, halogen light, etc. Annular light 24 emits visible light of frequency comparable to daylight. By way of non-limiting example, a suitable annular light can be a Stocker and Yale microscope illuminator with a White 5500HC fluorescent ring light having a color temperature of 5500 degree K, which produces a light close to Northern daylight. Light from annular light 24 is prevented from directly reaching diamond 20 by an annular baffle 28 disposed between the annular light 24 and the diamond 20. However, light from annular light 24 is reflected off a concave surface 26 of a reflector and generally towards diamond 20. The reflector can be a semi-spherical shell centered on the observation position with the inner surface of the shell being concave surface 26.

According to certain embodiments, the reflector can be mounted within the apparatus such that concave surface 26 can be rotatable about an axis 22 perpendicular to the platform and such that when diamond 20 is placed at the observation position, the centre of its table and its culet lie approximately along axis 22. Annular light 24 and annular baffle 28 are stationary and disposed within the apparatus such that they are also perpendicular to and centered around axis 22. A stepper motor (not shown) is provided for rotating the reflector, and concave surface 26, about axis 22.

It is appreciated that in further alternative embodiments, concave surface 26 can be held stationary within the apparatus, and instead the camera 30 and/or the platform can be rotated by a single or separate stepper motors in a separate or coordinated fashion. This arrangement can eliminate the need for extra processing to correct for the rotation of the images of diamond 20, but can involve additional mechanical complexity and increased cost of manufacture.

According to certain embodiments, a viewing hole 34 can be present at the bottom of the reflector and concave surface 26 where they meet axis 22. The digital camera 30 having a sensor array (e.g. a charged couple device (CCD) sensor array, a metal-oxide semiconductor (CMOS) sensor array, or any other suitable sensor array) can be positioned within the apparatus such that it can capture an image of diamond 20 along the axis 22. By way of non-limiting example, the camera can be a color camera having a fixed focal length, at least a 640*480 resolution, a memory capable of storing at least one image, and a data communication interface, compatible with standards such as, e.g., the Universal Serial Bus (USB), RS 422 parallel port or IEEE 1394 "Firewire" standards, for transferring captured image data to an external storing media (e.g. a memory 38-1 in computer 38 or in other external device). The camera 30 is focused on the plane made by the topmost surface of the platform on which diamond 20 is placed, and has a suitable depth of field such that sharp images can be captured of gemstones of the largest size reasonably expected to be measured. An optically clear mirror 32 can be disposed within the apparatus so that the light path between camera 30 and diamond 20 need not be a straight line, thereby enabling a more compact format of apparatus. By way of example, a suitable digital CCD camera can be a Unibrain Fire-i Digital CCD color camera with a resolution of 640*480 or a Unibrain Fire-i400 Industrial version with a similar resolution. A suitable digital CMOS camera can be a Silicon Imaging MegaCamera SI-3170 RGB camera, with a maximum resolution of 2056*1560, a 12-bit per pixel color depth.

One or more images of diamond 20 can be captured by the camera at one or more viewing angles (also termed as viewing points, or rotational positions) relative to the gemstone and to a light pattern of the concave surface 26. The camera is arranged to capture, at each of a plurality of rotational positions, an image of light returned by the gemstone and to output said images as image data. In some embodiments, the one or more viewing angles can be selected in accordance with the light pattern. In some cases, the one or more viewing angles can be evenly distributed with a predetermined range.

In some embodiments, the apparatus (including the light 24, baffle 28, reflector with concave surface 26, mirror 34, stepper motor, camera 30, and housing) can be compact in size. The apparatus can be calibrated or configured with respect to environment, such as, for example, illumination conditions.

Camera 30 and the stepper motor are controllable by a computer 36 operatively connected to the camera 30 and the stepper motor. By means of a suitable computer program, computer 36 controls the stepper motor to rotate concave surface 26 through a series of predetermined rotational positions as will be described in greater detail below. Control over the stepper motor can be achieved, for instance, by using a conventional stepper motor control circuit, such as a Motorola MC 3479 stepper motor, controller, to interface between computer 36 and the stepper motor and executing corresponding program elements on computer 36 for sending digital control signals to the stepper motor control circuit. Computer 36 also controls camera 30 to capture one or more images of diamond 20 at a suitable frame rate such that an image can be stored at each of the series of rotational positions of concave surface 26, for example, 45 images taken at rotational steps of 2 degrees over a total range of 90 degrees. Control over camera 30 can be achieved, for instance, by using the camera's inbuilt control interface and executing corresponding program elements on computer 36 for sending digital control signals to camera 30.

The series of images of diamond 20 can be captured and respective image data can be transferred from camera 30 to an external device for further processing and accommodation as further detailed with reference to FIGS. 5-9. For purpose of illustration only, in the following description processing of data informative of the captured images is provided by computer 38 operatively connected to camera 30. Those skilled in the art will readily appreciate that, likewise, the disclosed subject matter is also applicable for any other computer configured to obtain and process image data and not necessary operatively connected with the camera 30. It is also noted that functions of computer 36 and of computer 38 can be implemented within the same electronic device.

By way of non-limiting example, computer 38 can obtain the image data in the form of a bitmap or other suitable image file format for display and analysis. Optionally, camera 30 (or other computing device) can preprocess the captured images prior to obtaining image data by computer 38. In some embodiments the image data can be transmitted as a continual live image feed to the computer 38. Optionally, the image data (and/or derivatives thereof) can be stored in memory 38-1 of computer 38 and/or another memory operatively coupled to the apparatus.

According to certain embodiments, the image data can include data informative of a group of one or more images of the gemstone, wherein the images in the group are captured at different viewing angles relative to the gemstone and to a light pattern. As will be described in detail with respect to FIGS. 5-7, computer 38 can process, by a processing unit 38-2 comprised therein and operatively coupled to the memory 38-1, data informative of the images in the group to calculate a set of rotation-invariant values. Computer 38 further uses the generated set of rotation-invariant values to generate a unique identification associated with the gemstone and corresponding to the set of rotation invariant values.

The generated unique identification can be usable for unique identification of respective gemstones. Specifically, as will be described in detail below, two gemstones associated with two unique identifications are considered to be the same if a calculated matching score between the unique identifications meets a predefined criterion.

Optionally, but not necessarily so, generating, storing and comparing unique identifications can be provided by the same computer (e.g. computer 38). It is appreciated that functionality of computer 38 described herein can be implemented on a distributed device or system, which includes several functional components residing on different devices and controlled by a control layer as a virtual entity to perform the operations described herein. By way of non-limiting example, the I/O interface and/or the memory can reside on a local computer, while the processing unit or part of the functional components thereof can reside on a remote server for performing the processing and/or the calculation. In addition, the processing unit and/or memory can in some cases be cloud-based.

Those versed in the art will readily appreciate that, likewise, the disclosed functions of computer 38 can be implemented on a plurality of computers, some of which can operate independently from the others. Optionally, the computers of the plurality of computers can operate in a cloud environment. For example, unique identifications for different gemstones can be generated by different computers and at different time. Such computers can, optionally, be different and independent of computers involved in generation of unique identification. Unique identifications can be stored in one or more databases accessible to a computer providing gemstone identification.

Figure 3A:
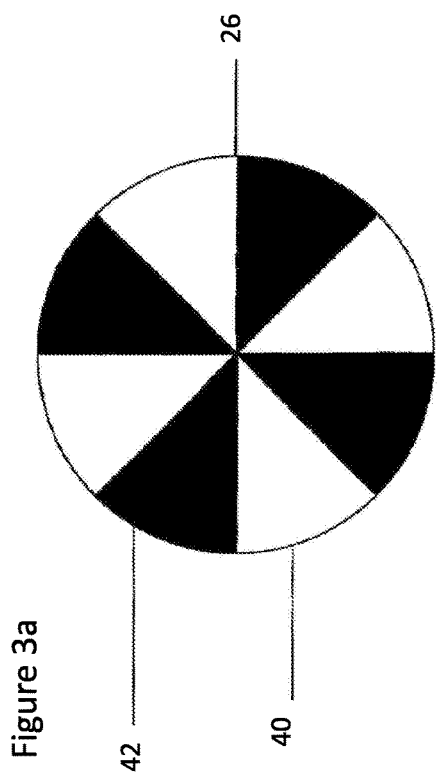
FIGS. 3a and 3b illustrate the concave surface of the apparatus of FIG. 2 having exemplary light patterns of relatively reflective and relatively unreflective regions in accordance with certain embodiments of the presently disclosed subject matter.
Figure 3B:
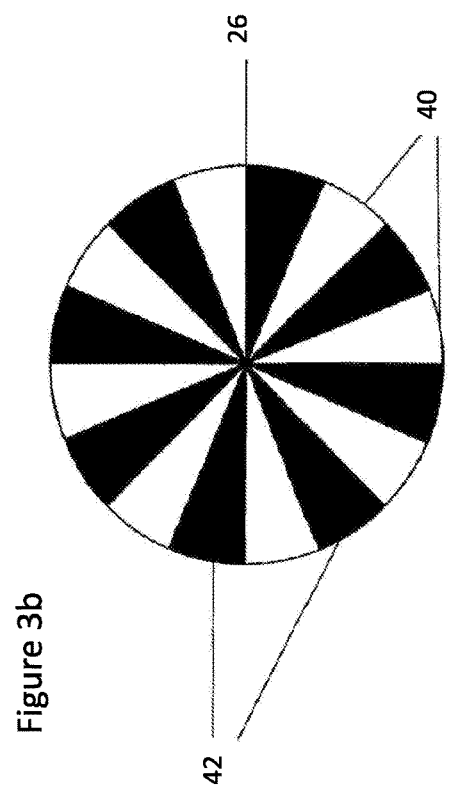

FIGS. 3a and 3b illustrate the concave surface of the apparatus of FIG. 2 having exemplary light patterns of relatively reflective and relatively unreflective regions in accordance with certain embodiments of the presently disclosed subject matter.

The concave surface 26 is shown as looking down from the diamond observation position along axis 22. Concave surface 26 is configured to have a light pattern. The light pattern can be uniformly light, e.g., the whole pattern including only one light region. Alternatively, the light pattern can comprise one or more relatively reflective regions (e.g., relatively light regions) 40 and one or more relatively unreflective regions (e.g., relatively dark regions) 42 formed by coating the surface with relatively reflective and relatively unreflective materials. FIG. 3a shows exemplified configuration of regions 40 and 42 in which concave surface 26 is divided into eight equal radial sectors, arranged around the axis 22, which are alternately relatively reflective and relatively unreflective. FIG. 3b shows another non-limiting example of configuration of regions 40, 42 in which concave surface 26 is divided into 16 equal sectors, arranged around the axis 22, of alternate relatively reflective and relatively unreflective regions. It can be seen that in the configuration in FIG. 3a regions 40 and 42 each have a four-fold symmetry about the axis 22, whereas in the configuration in FIG. 3b regions 40 and 42 each have an eight-fold symmetry about axis 22.

It is to be noted that the above described light patterns are illustrated for exemplary purposes only and should not be construed to limit the present disclosure in any way. Other configurations of relatively reflective regions 40 and relatively unreflective regions 42 can be applied in lieu of the above. Optionally, concave surface 26 can have a matt finish, polished finish, combined finish, etc.

During operation of the apparatus, it can be seen that the light reflecting off concave surface 26 towards the diamond 20 at its observation position has a spatially varied pattern determined by the configuration of relatively reflective regions 40 and relatively unreflective regions 42. In particular, the reflected light pattern, as observed in the plane of the platform, will have a series of radial peaks and troughs of light intensity corresponding to the configuration. Thus, for example, with the configuration of FIG. 3a, the reflected light pattern will have four radial peak lines and four radial trough lines. Similarly, with the configuration of FIG. 3b, the reflected light pattern will have 8 radial peaks and 8 radial troughs. Furthermore, with diamond 20 table-side down on the platform, the light will be reflected generally towards the crown at a broad range of angles of incidence relative to axis 22, as predominantly occurs when diamonds are mounted in rings and other jewelry for everyday use.

According to certain embodiments, the selection of a particular configuration of a light pattern of relatively reflective regions 40 and relatively unreflective regions 42 can be dependent upon a cut of the gemstone. For example, a diamond of RBC cut has an eight-fold symmetry as described above, and a suitable configuration of regions 40 and 42 would be that as shown in FIG. 3a, in which there are eight sectors in total: four relatively reflective sectors 40 and four relatively unreflective sectors 42. Thus, the light pattern reflecting off concave surface 26, having four radial peaks and four radial troughs, corresponds to the symmetry of the cut gemstone, in that adjacent symmetrical sectors of the gemstone (of 45 degrees) will receive corresponding radial light pattern sectors (of 45 degrees) having adjacent peaks and troughs. As concave surface 26 is rotated through 90 degrees, the intensity of light as observed at any radial line in the plane of the platform and about axis X, will go through a single complete cycle having a single peak and a single trough.

It is appreciated that, with different shapes and/or symmetries of particular gemstone cut patterns, such as square, oval, pear, heart-shaped or irregular shapes, the configuration of a light pattern of relatively reflective regions 40 and relatively unreflective regions 42 of concave surface 26, can be varied to take into account the shape and symmetry of the particular gemstone cut pattern. It is also to be appreciated that the configuration of relatively reflective regions 40 and relatively unreflective regions 42 of concave surface 26 can be varied to take into account a particular unique identification to be determined.

While the above embodiment has described an apparatus arranged to i) support a gemstone having an axis of symmetry such that the axis of symmetry is parallel to the axis 22, ii) rotate the light pattern relative to the platform about the axis 22, and iii) capture images of the gemstone along the axis 22, it is to be noted that the present disclosure is not limited to this particular arrangement of the three axes. In particular, the axis of relative rotation between the light pattern and the platform need not be co-linear or even parallel to the axis 22 (i.e. from the axis parallel to an axis of symmetry of a gemstone when supported in the apparatus) and/or the axis along which the images are captured need not be co-linear or even parallel to the axis 22. Furthermore, the axis of relative rotation between the light pattern and the platform and the axis along which the images are captured need not be co-linear or even parallel between themselves.

According to certain embodiments, a gemstone having an axis of symmetry can be supported in the apparatus such that the axis of symmetry, the axis of relative rotation between the light pattern and the means of support, and the axis along which the images are captured are coordinated such that i) the apparatus is able to take advantage of the shape and/or symmetry of the cut pattern of the particular gemstone when rotating the light pattern relative to the gemstone, and ii) the apparatus is able to capture images of the gemstone, such as images of the crown of a RBC diamond, from which features resulting from the shape and/or symmetry of the gemstone can be observed. For instance, the axis of relative rotation between the light pattern and the means of support can be at an angle of incidence to the axis of symmetry of up to about 30 degrees without serious degradation to the performance of the apparatus. Similarly, the axis along which the images are captured can be at an angle of incidence to the axis of symmetry of up to, e.g., about 45 degrees without serious degradation to the performance of the apparatus.

Figure 4A:
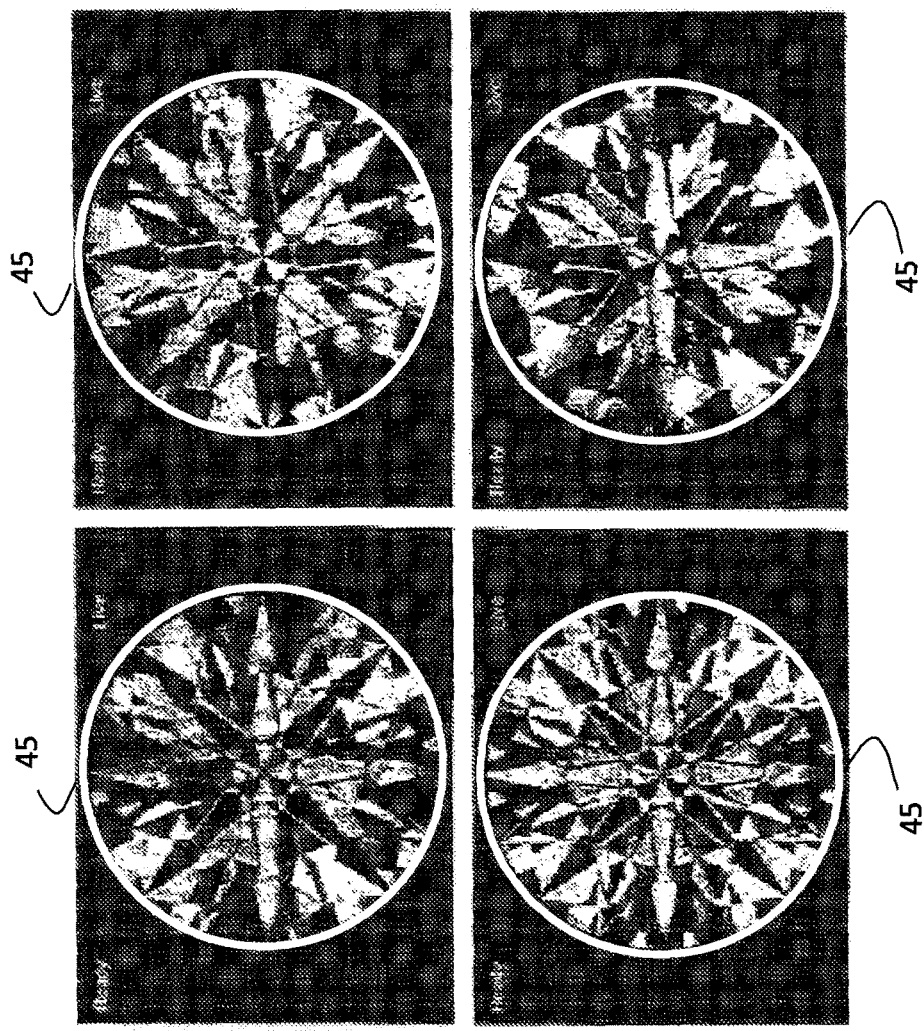
FIG. 4a illustrates four exemplified images of a cut diamond captured at different rotational positions each shown with a circumference of the diamond and a center point of the diamond in accordance with certain embodiments of the presently disclosed subject matter.

Referring to FIG. 4a, there are illustrated four exemplified images of a cut diamond captured at different rotational positions of the same light pattern. Each image is shown with a circumference 45 (added to the images for the sake of clarity) of a diamond with a center in a center point of the diamond image. It can be seen that various geometrical patterns of light and dark regions are formed and, in different rotational positions, the regions appear either relatively light or relatively dark.

It is to be appreciated that, with different shapes and/or symmetries of particular gemstone cut patterns, such as square, oval, pear, heart-shaped or irregular shapes, the techniques used to determine the periphery of the gemstone and the various measurements of optical properties, as described above, can be varied to take into account the shape and symmetry of the particular gemstone cut pattern.

Figure 5:
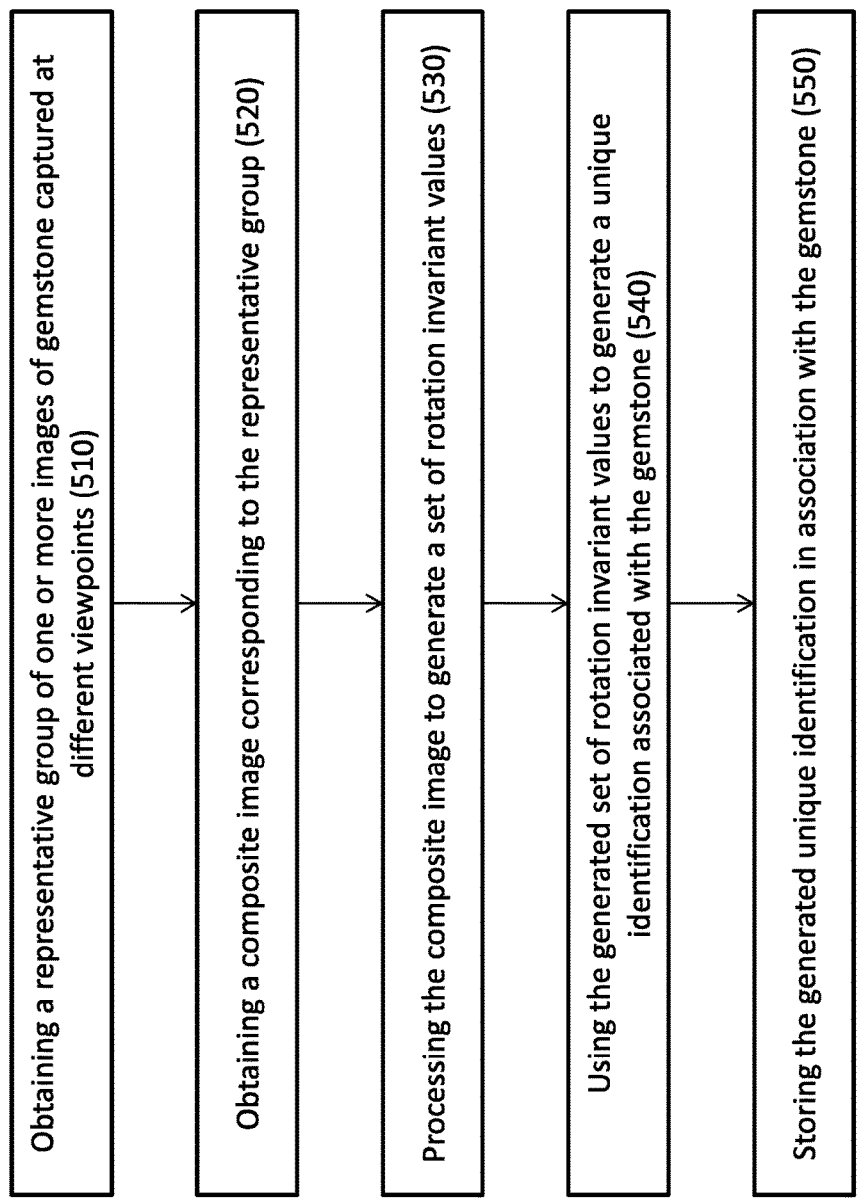
FIG. 5 illustrates a generalized flowchart of generating a unique identification associated with a gemstone in accordance with certain embodiments of the presently disclosed subject matter.

Having described the apparatus capable of scanning the gemstone and generating image data usable for determining a unique identification associated with a gemstone, attention is now directed to FIG. 5, schematically illustrating a generalized flowchart of generating a unique identification associated with a gemstone in accordance with certain embodiments of the presently disclosed subject matter.

Computer 38 obtains (510) data informative of one or more images captured for the gemstone, thereby giving rise to a representative group of images. As aforementioned with respect to FIG. 2, the captured images of the gemstone are reflection based images (e.g., reflected by the concave surface 26 of the reflector) captured by a machine. A representative group of images comprises images captured at one or more viewing angles (also referred to as viewpoints or rotational positions) relative to the gemstone and to the light pattern of the concave surface 26. According to certain embodiments, the one or more viewing angles can be selected in accordance with the light pattern. In some cases, the one or more viewing angles can be evenly distributed within a predetermined range. The images can be captured from a direction perpendicular to the gemstone's table.

The range of viewing angles selected for a representative group of images is dependent upon the symmetry of the light pattern reflecting off concave surface 26, the symmetry of the light pattern corresponding to the symmetry of the gemstone. With a light pattern having a 4-fold symmetry, for example, images in the representative group are captured at a plurality of rotational positions as concave surface 26 is rotated through a range (e.g., 90 degrees). Within the range, the number of images in the representative group captured at different rotational positions is defined by the cut pattern of the gemstone being measured, or the cut pattern of the most faceted gemstone likely to be measured. In some embodiments, the number of images in the representative group should be at least 4 times the number of differently angled facets within the range through which concave surface 26 is rotated. Thus, with a RBC diamond having 32 differently angled facets in its crown and pavilion and thus 8 differently angled facets within a 90 degree range, the representative group shall include at least 32 images (4*8) over the 90 degree range. In certain embodiments, concave surface 26 can be rotated over a 90 degree range in steps of 2 degrees, thus a representative group for such a diamond includes 45 images, each captured in steps of 2 degrees. It will be understood that higher or lower numbers of images can be used as appropriate to the cut pattern of the gemstone, the accuracy of measurement required, and the processing capabilities of the computer.

The machine that captures the images (e.g., the apparatus described with respect to FIG. 2) can be calibrated with respect to the environment (e.g. illumination conditions, camera settings, for example exposure and gain, optical path of the light, etc.) in order to provide consistently repeatable conditions for capturing images. At least, due to such calibration, the images captured by the machine can provide relatively accurate representations of a gemstone regardless of time, location and machine used for the image acquisition. In certain embodiments, all images in the representative group shall be captured during the same scan of the gemstone. In alternative embodiments, the representative group can comprise images captured during different scans using the same light pattern or light patterns of equivalent configuration. A light pattern can be considered to have an equivalent configuration, as long as it was rotated in a range of angles according to its symmetry, as described above.

According to certain embodiments, computer 38 can receive data informative of the images in the representative group directly from camera 30. Alternatively or additionally, data informative of at least part of the images in the representative group can be pre-stored in a memory of computer 38 and obtained therefrom. In some other cases data informative of at least part of the images in the representative group can also be received from a memory external for computer 38 and accessible therefor (e.g. in a cloud architecture).

Figure 4B:
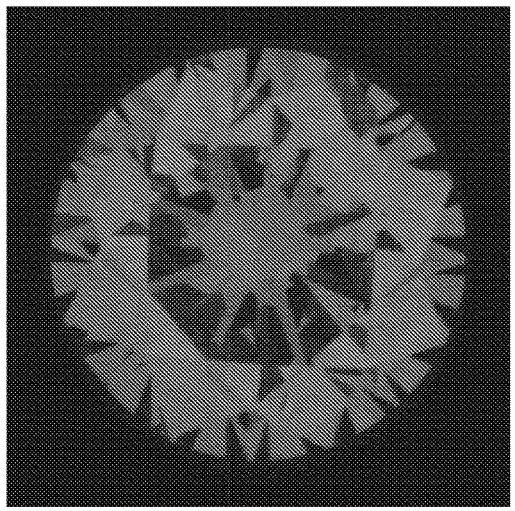
Figure 4C:
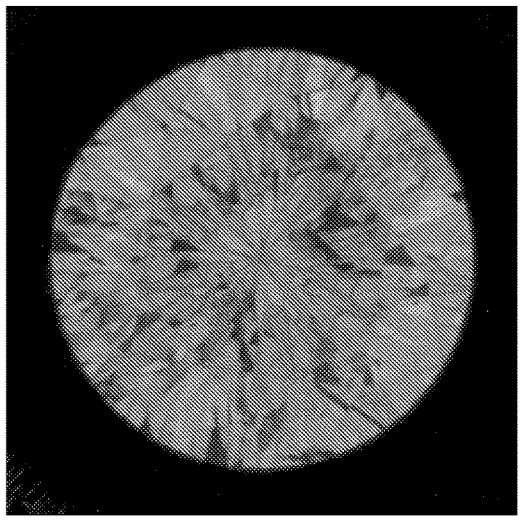

Computer 38 processes the images in the representative group to generate a composite image corresponding to the images in the representative group. The composite image is generated by combining data informative of the captured images in the representative group. For instance, the computer can generate the composite image based on a non-weighted average of pixel values over the images in the representative group. For the representative group of images illustrated in FIG. 4, a composite image obtained using non-weighted average scheme is illustrated in FIG. 4b and a composite image obtained using weighted average scheme is illustrated in FIG. 4c. Optionally, at least part of the images in the representative group can be processed prior to generating the composite image and the composite image can be generated based on the post processed versions of such images. If the representative group comprises only one captured image, the composite image can be this captured image itself.

The pixel values referred to therein should be expansively construed to cover any suitable kind of representation of variation of pixels in any kind of color model or color space. In some embodiments, lightness values of pixels that represent relative lightness and darkness of a color can be used. It is noted that different color models can have different representations for lightness of pixels. Some color models have a separate channel to represent lightness, for example, the Y channel in YUV color model, the V channel in HSV color model, etc. Some color models, such as RGB, although they do not have a separate channel for it, can provide representation for lightness in different ways, or can be converted to another color model in order to obtain such lightness values. By way of example, if the one or more images of the gemstone are captured in RGB format, these RGB images can be converted to, e.g., HSV representations, after which the V channel values for each pixel over all the images are merged together into a single grayscale image using a weighted average, giving rise to the composite image.

For purpose of illustration only, in the following description generating unique identification is detailed for data informative of a composite image of the representative group. Those skilled in the art will readily appreciate that, likewise, the teachings disclosed herein are applicable for processing individual images (and/or groups thereof) in the representative group with further composing of the individual results.

Upon obtaining (520) the composite image, computer 38 processes the composite image to generate (530) a set of rotation invariant values characterizing the gemstone. Obtaining the composite image can comprise generating it by processor 38-2 or receiving the composite image from memory 38-1 or a remote memory (e.g. $3^{rd}$ party database). The set of rotation-invariant values is informative of rotational cross-correlation relationship characterizing the images in the representative group. The term "rotation-invariant" is used herein to indicate that such values are independent of specific rotation conditions, e.g. the rotation of the gemstone with respect to the light environment, etc.

It is noted that cross-correlation can be defined in spatial domain, in frequency domain, or using other correlation metrics.

The computer calculates the rotational cross-correlation relationship between the composite image and respective rotated images of the composite image. The respective rotated images are rotation versions of the composite image within a predetermined span of degrees. In some cases, the rotation versions can be evenly spaced within the predetermined span. By way of non-limiting example, within a predetermined span of 180 degrees, the composite image can be rotated every 0.5 degrees, giving rise to 360 rotated images of the original composite image. A cross-correlation value can be computed between the composite image and each rotated image. Such calculation can be provided by multiplying in spatial domain the composite image with each of the 360 rotated images, by multiplying in the frequency domain, or by using other correlation metrics instead. The calculation results in a set of rotation-invariant values including 360 cross-correlation values, each corresponding to their respective multiplication. It is to be noted that the above predetermined span of 180 degrees and the interval of 0.5 degrees between rotated images are illustrated for exemplary purposes only and should not be construed to limit the present disclosure in any way. According to certain embodiments, the predetermined span of degrees and the number of rotated images can be determined at least based on a resolution parameter and an accuracy parameter. The resolution parameter can be indicative of the resolution configuration of the captured images and/or the composite image. The accuracy parameter can indicate the accuracy level required for the scanning and/or identification of the gemstone.

Optionally, prior to generating the set of rotation-invariant values, the computer can process the composite image to define the location (e.g., the center point of the gemstone) and size (e.g., the circumference of the gemstone) of an image area corresponding to the gemstone, and further use the defined gemstone image area when calculating the rotation-invariant values. Defining the gemstone image area can be provided by means of any suitable edge detection algorithm. By way of non-limiting example, a plurality of pixels on the composite image with a pixel value (e.g., a lightness value) above a predetermined threshold can be selected, such pixels representing a lightness level slightly above the level of the black background. A circle area containing the selected pixels can be determined, e.g., by matching the boundary of the selected pixels with a minimal-square-distance circle. The determined circle area is defined as the gemstone image area on the composite image corresponding to the gemstone.

The computer further uses the set of rotation invariant values to generate (540) a unique identification associated with the gemstone.

Unique identification can be configured in the form of any data object informative of the generated set of rotation invariant values and suitable for comparing different sets of such values. By way of non-limiting example, unique identification can be configured as a curve representing rotation-invariant values obtained for cross correlations between the composite image and different rotations thereof.

Figure 6A:
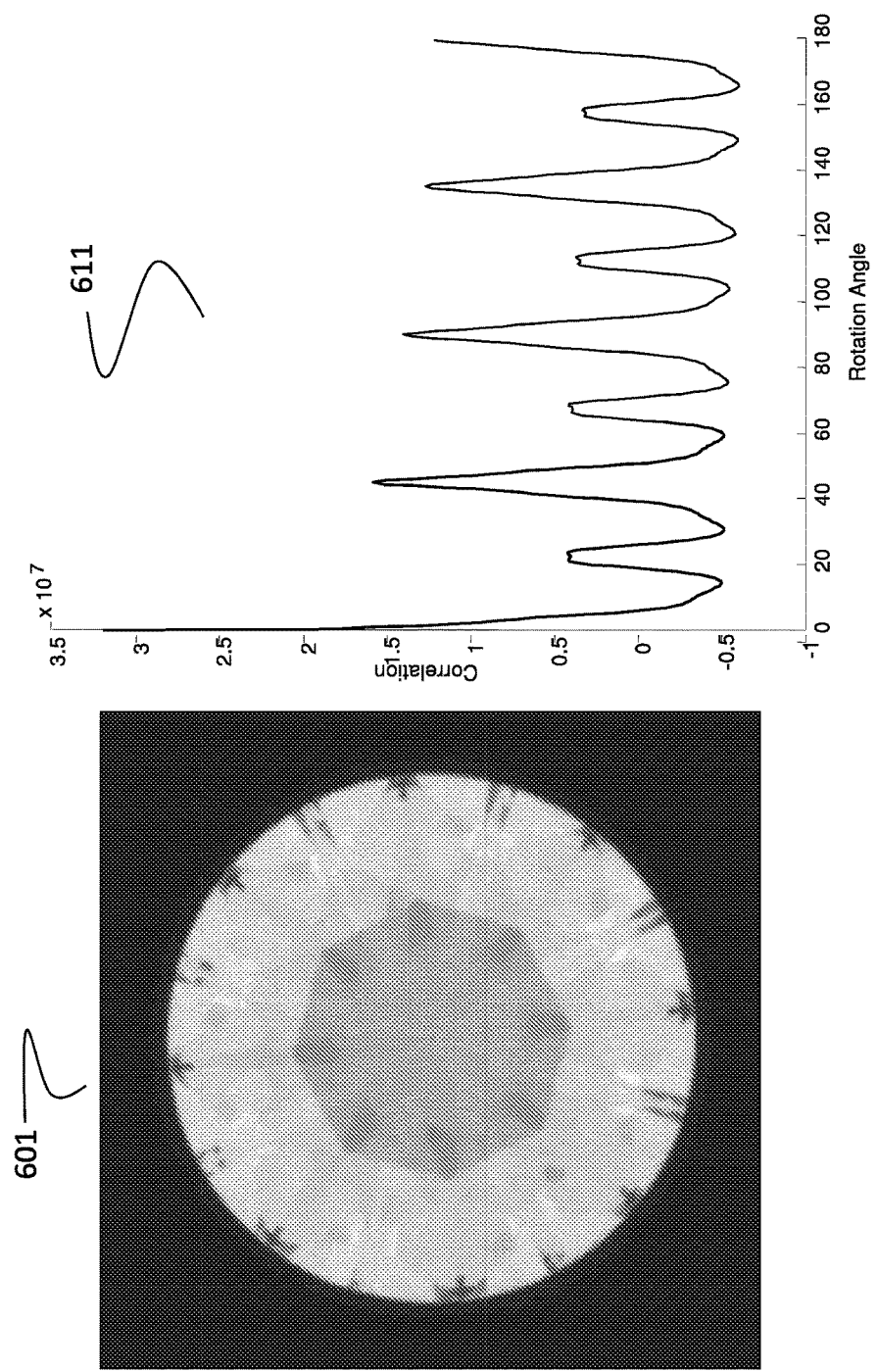
FIG. 6a illustrates an exemplified composite image of a first gemstone and a unique identification calculated based on a composite image of the first gemstone in accordance with certain embodiments of the presently disclosed subject matter.
Figure 6B:
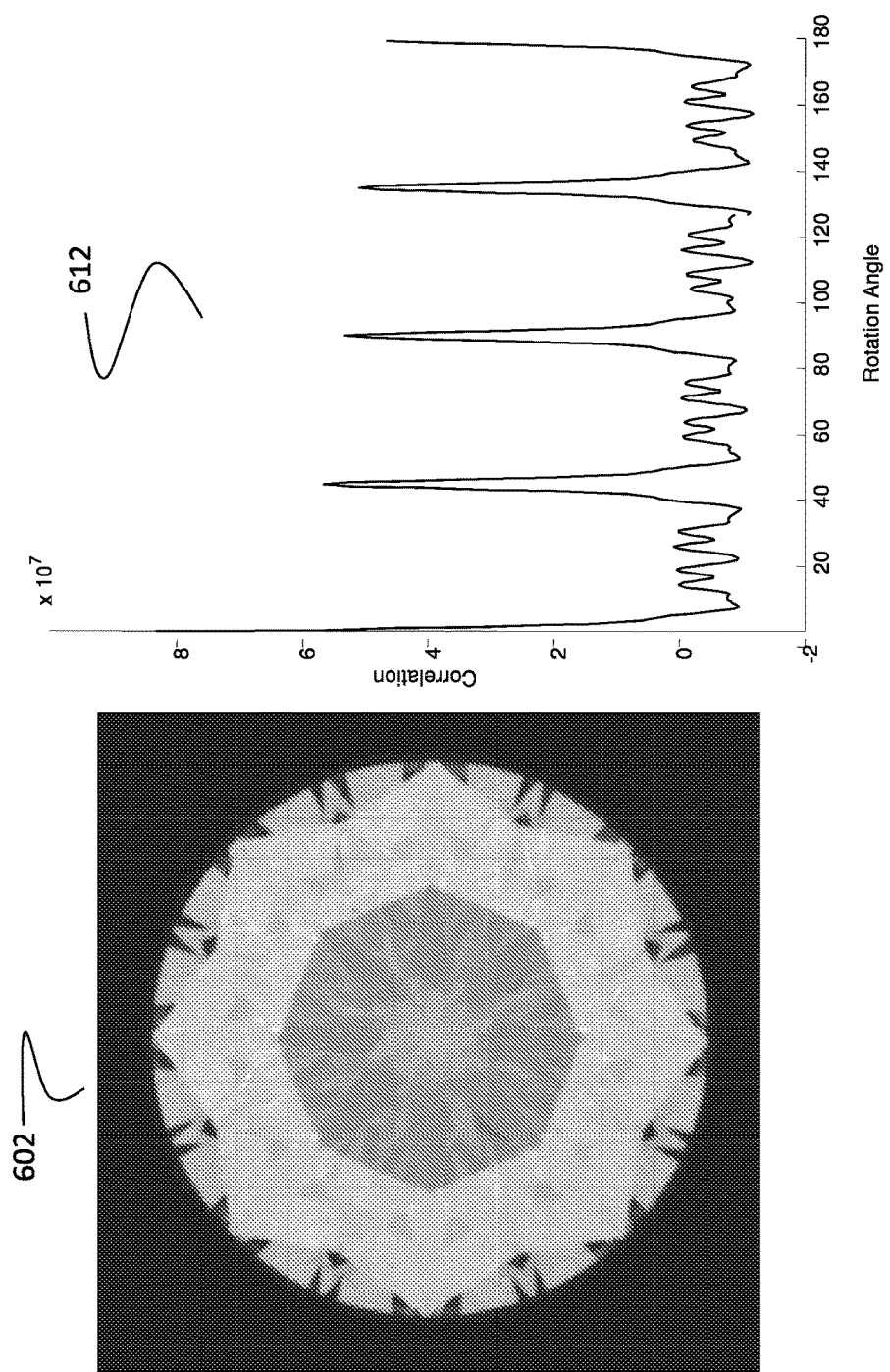
FIG. 6b illustrates an exemplified composite image of a second gemstone and a unique identification calculated based on a composite image of the second gemstone in accordance with certain embodiments of the presently disclosed subject matter

Non-limiting examples of unique identification are illustrated with reference to FIGS. 6a and 6b. FIG. 6a illustrates an exemplary composite image 601 of a first gemstone and a unique identification 611 calculated based on the composite image 601 in accordance with certain embodiments of the presently disclosed subject matter and associated with the first gemstone. The first gemstone has been scanned by different apparatuses to obtain several composite images thereof. For any given composite image among these composite images, a set of cross-correlation values calculated for rotation angles within a span of 180 degrees substantially corresponds to the curve 611 obtained for the image 601. Thus, the curve 611 generated for the first gemstone in accordance with certain embodiments of the presently disclosed subject matter is unique to the first gemstone across different scans and machines and is usable as a unique identification associated with the first gemstone. Similarly, FIG. 6b illustrates an exemplary composite image 602 of a second gemstone and a unique identification 612 calculated based on the composite image 602 and associated with the second gemstone. The illustrated composite images 601 and 602 have been obtained by non-weighted averaging images in respective representative groups, and then by extracting the lightness channel in a manner described above with reference to FIGS. 4b and 4c.

By way of another non-limiting example, unique identification can be configured as a function (e.g. hash function) calculated in accordance with the set of rotation-invariant values obtained from the representative group of images. Optionally, calculating of such functions can be provided in accordance with additional values characterizing the gemstone (e.g. size, shape, color, etc. and/or values obtained from the representative group of images and not included in the set of rotation-invariant values).

Referring back to FIG. 5, the generated unique identification can be further stored (550) in the memory 38-1 of computer 38 and/or can be further transferred to other electronic devices for storing and/or processing. The unique identification can be stored in association with a respective gemstone (e.g. referring to the gemstone's commercial identification data).

Figure 7:
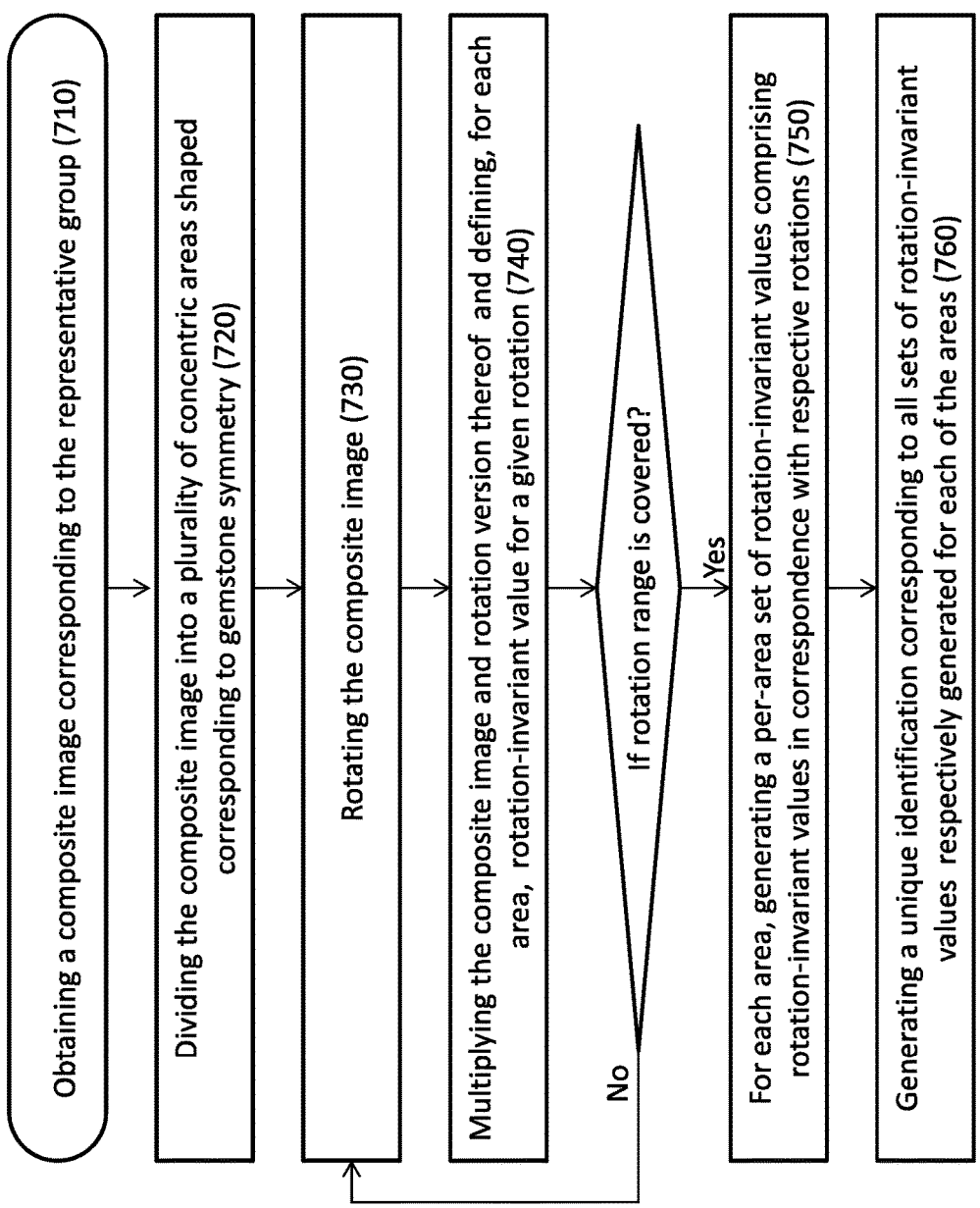
FIG. 7 illustrates a generalized flow-chart of an exemplified embodiment of generating a unique identification associated with a gemstone in accordance with certain embodiments of the presently disclosed subject matter.

A flowchart of exemplary generation of unique identification associated with a gemstone is illustrated in FIG. 7.

Upon obtaining (710) a composite image, computer divides (720) the composite image (or, optionally, only gemstone image area thereof) into a plurality of concentric areas. The shape of concentric areas corresponds to the shape of the respective gemstone (e.g. concentric rings for round diamonds illustrated in FIG. 1 or any other gemstone with round shape; concentric squares for Princess-shape diamonds; etc.). The division can be provided in different ways. For instance, the concentric rings can have equal areas, or alternatively, can have equal radii.

Figure 4D:
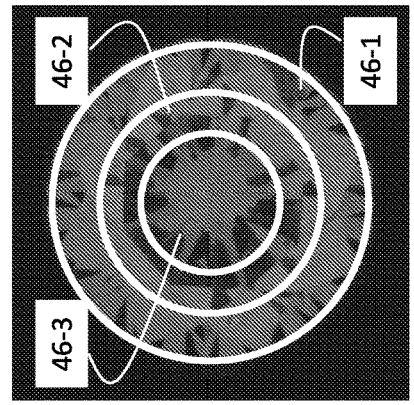
Figure 4E:
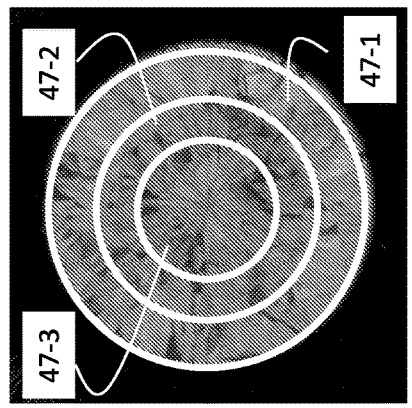

By way of non-limiting example, FIG. 4d illustrates the composite image illustrated in FIG. 4b and divided into rings 46-1, 46-2 and 46-3; FIG. 4e illustrates the composite image illustrated in FIG. 4c and divided into rings 47-1, 47-2 and 47-3.

For each of the concentric areas, the computer rotates (730) the composite image, and calculates rotational cross-correlation value between the composite image and respective rotation version, thereby defining (740) rotation-invariant value for a given rotation. By way of non-limiting example, rotation-invariant value for a given rotation can be calculated by multiplying the composite image with the respective rotation version. Operations 730 and 740 are repeated to obtain rotation-invariant values for all required rotations (e.g. evenly distributed with 1 degree interval) over a predefined rotation range (e.g. 180 degrees).

It is noted that rotation-invariant values for all required rotations and/or for each of the concentric areas can be calculated in any suitable order.

The computer further generates (750), for each given concentric area, a set of rotation-invariant values. The set generated for a given area comprises rotation-invariant values defined for the given area in correspondence with respective rotations, and represents the cross-correlation relationship between the given area and its rotated versions at different rotation angles. Upon the calculation for all areas being completed, the computer generates (760) unique identification of the gemstone, the unique identification corresponding to all per-area sets of rotation-invariant values respectively generated to each of the concentric areas.

It is noted that the teachings detailed with reference to FIG. 7 are applicable in a similar manner when the composite image is divided in non-concentric areas enabling tessellated coverage of the image. It is also noted that the described with reference to FIG. 7 dividing the composite image into the areas is optional, and unique identification can be generated based on processing the composite image as whole or based on processing individual images (and/or groups thereof) in the representative group with further composing of the individual results.

It is also to be noted that the procedure described with reference to FIG. 5 and FIG. 7 with respect to the composite image can be carried out through other analogous methods of rotating the representative group of images, such as, but not limited to, the Mellin transform. It can be understood that these alternatives, although procedurally different, are functionally equivalent and as such are covered by the currently disclosed subject matter.

Figure 8:
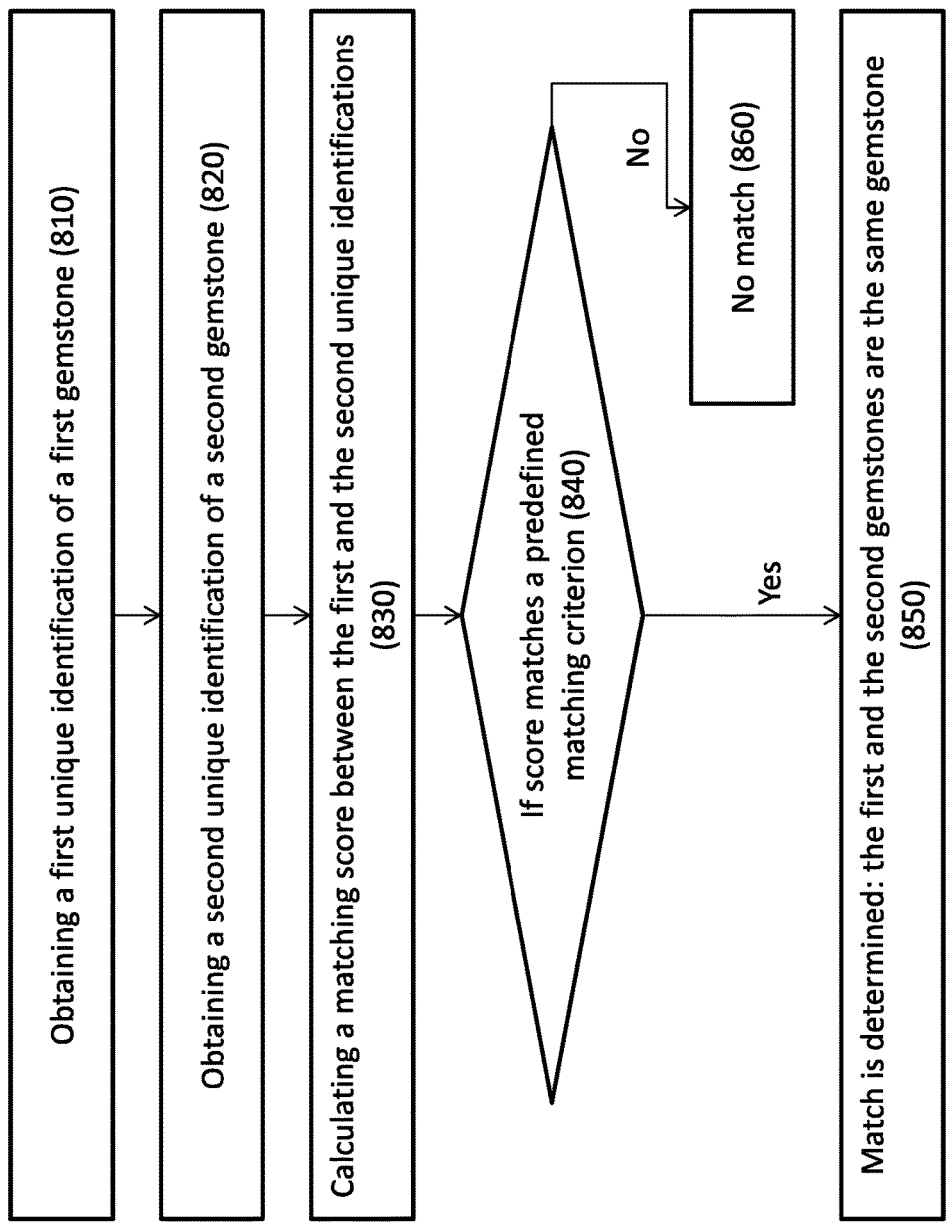
FIG. 8 illustrates a generalized flowchart of uniquely identifying a gemstone in accordance with certain embodiments of the presently disclosed subject matter.

Attention is now directed to FIG. 8, schematically illustrating a generalized flowchart of uniquely identifying a gemstone in accordance with certain embodiments of the presently disclosed subject matter.

Computer 38 obtains (810) a first unique identification associated with a first gemstone and obtains (820) a second unique identification associated with a second gemstone. The first and the second unique identifications can be generated as detailed with reference to FIGS. 5 and/or 7. Specifically, the first unique identification is informative of a first set of rotation-invariant values informative of rotational cross-correlation relationship characterizing a first representative group of images captured at one or more viewing angles relative to the first gemstone and to a first light pattern. The second unique identification is informative of a second set of rotation-invariant values informative of rotational cross-correlation relationship characterizing a second representative group of images captured at one or more viewing angles relative to the second gemstone and to a second light pattern. Optionally, the second light pattern can differ from the first light pattern. Optionally images in the first and the second representative groups can be captured with different distribution of viewing angles.

It is noted that the first unique identification and/or the second unique identification can be generated in advance, pre-stored and be later obtained from the storage location(s). The first unique identification and/or the second unique identification can be pre-stored in computer 38 and/or in a remote memory, including a memory implemented in a cloud environment (e.g. in a $3^{rd}$ party database).

Alternatively, the first unique identification and/or the second unique identification can also be generated on-demand instead of being pre-stored.

It is further noted that the apparatus that scans the first gemstone and the apparatus that scans the second gemstone can be the same machine, or, alternatively, they can be different machines calibrated with regard to environmental conditions. The first unique identification and the second unique identification can be generated by the same computer, or can be generated by different computers optionally located at different locations.

It is further to be noted that the order of obtaining the first unique identification and the second unique identification is not fixed and can be interchangeable, or alternatively the two unique identifications can be obtained simultaneously.

Computer 38 further calculates (830) a matching score for the first and second unique identifications. The matching score can be a one-dimensional or multi-dimensional cross-correlation score. In some cases, the cross-correlation score can further be normalized.

As aforementioned, each unique identification can comprise a set of rotation-invariant values. One-dimensional cross-correlation between the first and second unique identifications can result in a numerical cross-correlation score indicating the level of similarity between these two respective sets. By way of non-limiting example, in a case of unique identifications generated as a curve representing rotation-invariant values obtained for different rotation angles, the cross-correlation score can be a derivative of scores calculated for each of the rotation angles.

The computer determines (840), in accordance with the matching score, if the first unique identification matches the second unique identification. The first gemstone associated with the first unique identification can be determined as being the same to the second gemstone associated with the second unique identification when the matching score meets a predefined matching criterion (850). If the matching score does not meet the predefined matching criterion, it is determined that there is no match (860) between the two gemstones. The predefined matching criterion can be a threshold determined based on, for example, experimental results and previous experiences.

Optionally, when each unique identification comprises a plurality of area-based sets of rotation-invariant values (e.g. as detailed with reference to FIG. 7), calculating the matching score can comprise calculating matching scores for each pair of corresponding areas in respective composite images. Referring by non-limiting example, to FIGS. 4d-4e, matching score can be calculated for the pairs of rings 46-1/47-1, 46-2/47-2 and 46-3/47-3. By way of non-limiting example, a match can be determined when a normalized cross-correlation score of each pair meets a respective predefined criterion. Optionally, such a criterion can be predefined differently for different areas. The gemstones can be considered as different when at least one pair of areas has a cross-correlation score that does not meet the predefined criterion. By way of another non-limiting example, a match can be determined when a certain function of matching scores calculated for all pairs meets a predefined matching criterion.

It is noted that the first and the second unique identifications can be generated as data objects of different structures. If so, the first and the second unique identifications can be transformed into a common form before comparing.

However, in order to be comparable, the first unique identification and the second unique identification shall be generated by the same or by equivalent techniques enabling compatibility of the first and the second identifications. The techniques of generating unique identifications are considered as equivalent if they enable a compatible structure of the set of rotation-invariant values measured at the same scale (e.g. from "−1" to "1" after normalization).

By way of non-limiting examples, the techniques can be considered equivalent when:

the unique identifications have been generated using different light patterns (the respective composite images will still be substantially identical, and thus the sets of rotation-invariant values will have the same structure and are compatible);

one unique identification has been generated based on a gemstone image area, while the other has been generated based on the entire image (the sets of rotation-invariant values will have different noise levels but the same structure, and are thereby compatible);

the unique identifications have been generated using different distribution and/or a number of rotation positions within a predefined range, or using different predefined ranges (although the sets of rotation-invariant values will initially be of different dimensions, applying interpolation can enable the same structure and, accordingly, compatibility of the sets).

By way of non-limiting examples, the techniques can be considered as non-equivalent when:

one unique identification has been generated based on cross-correlation in a frequency-domain while the other has been generated based on cross-correlation in a spatial domain (the respective sets are not compatible);

the two unique identifications have been created using a different number of concentric rings (the sets of rotation-invariant values will be constituted by different numbers of per-ring rotation-invariant sets representing incompatible measurements).

However, it is noted that if the second unique identification is generated using further subdivision of the same concentric rings as have been used for the first unique identification, the techniques of generating these unique identifications are considered as equivalent as the second set can be equivalently transformed into the first set.

It is also noted that the techniques of generating two unique identifications by using the same number of concentric rings but with different sizes or shapes (e.g. rings used for the first unique identification have equal area, and rings used for the second unique identification have equal radii) are considered as equivalent as the second set can be equivalently transformed into the first set.

Referring back to FIGS. 6a and 6b, the two illustrated gemstones have distinct composite images 601 and 602 resulting from different characteristics (e.g., roughness, cut, quality, etc.) of the gemstones. Two curves 611 and 612, representing respective unique identifications associated with these gemstones, appear to be different with a cross-correlation score not matching a predefined criterion. Thus it is rendered that the unique identification generated for a gemstone in accordance with the above description is unique to a gemstone in question across different scans and machines, and enables distinguishing one gemstone from another.

Figure 9:
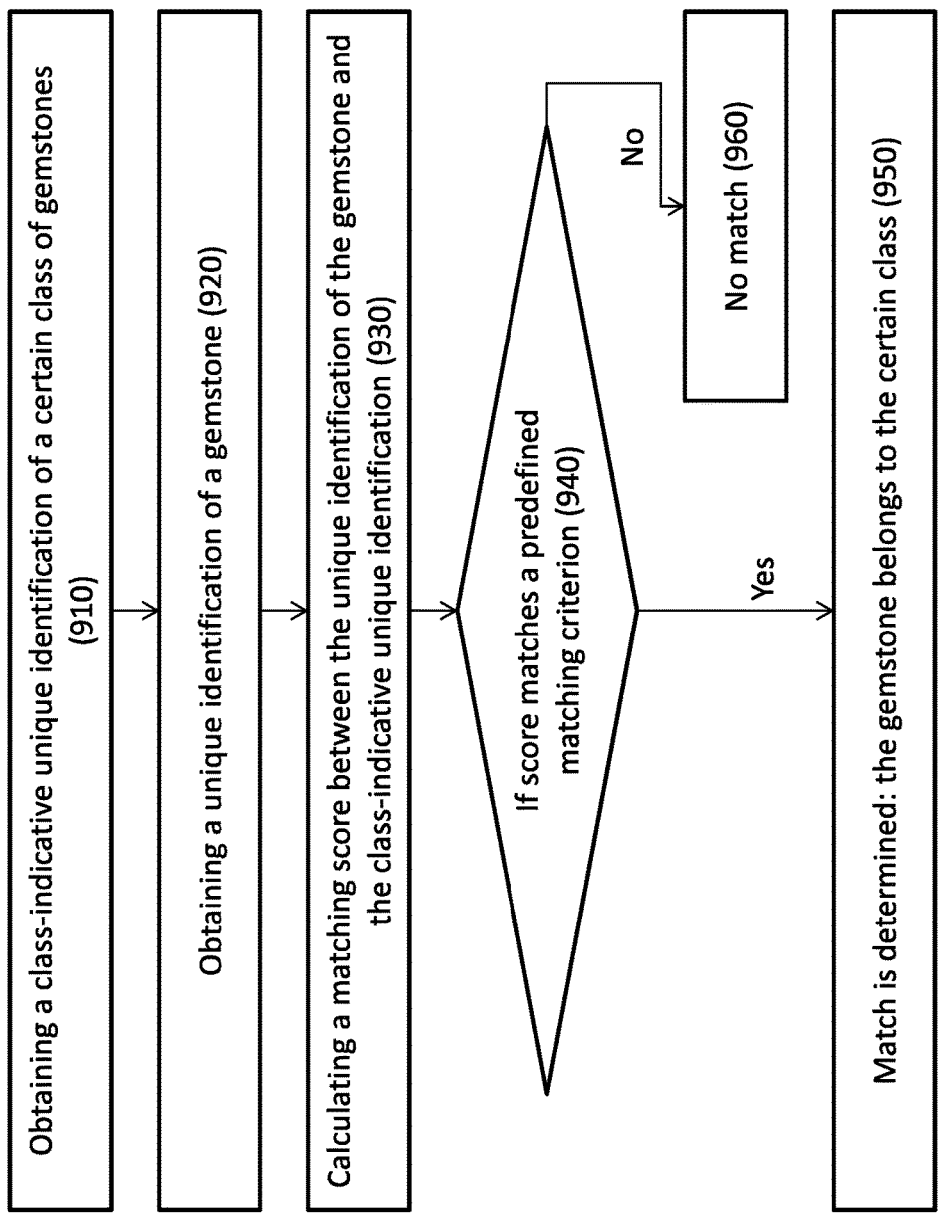
FIG. 9 illustrates a generalized flow-chart of identifying a gemstone belonging to a certain unique class of gemstones in accordance with certain embodiments of the presently disclosed subject matter.

In accordance with further embodiments of the presently disclosed subject matter, a unique identification of a given gemstone can be also usable for identifying the certain class of gemstones to which the given gemstone belongs. A class of gemstone is characterized by a certain range of values for parameters (e.g. shape, and/or cut, and/or color, and/or fluorescence, etc.) of gemstones belonging to the class. A generalized flowchart of unique identifying of belonging a given gemstone to a certain class is illustrated in FIG. 9.

In a manner similar as detailed with reference to FIG. 8, upon obtaining (910) a class-indicative unique identification and obtaining (920) a unique identification of a given gemstone, the computer calculates (930) a matching score between the unique identification of the gemstone and the class-indicative unique identification.

A given class of gemstones can be associated with a reference class-indicative unique identification. The reference class-indicative unique identification can be generated for a "reference" gemstone representing the given class. Alternatively or additionally, class-indicative unique identification associated with a given class can be generated using statistical data resulting from processing representative groups of images obtained for a statistically reliable amount of gemstones corresponding to the given class. Class-indicative unique identification can be generated in a manner similar to generation of the unique identification as detailed with reference to FIG. 5 and/or FIG. 7.

Comparing unique identification associated with a given gemstone with a class-indicative unique identification associated with a given class enables identifying the given gemstone as belonging (or not belonging) to the given class. The unique identification associated with the gemstone and the class-indicative unique identification shall be generated by the equivalent techniques enabling compatibility of the unique identifications.

The computer determines (940), in accordance with the matching score, if the unique identification associated with the given gemstone matches the class-indicative unique identification associated with the given class. The given gemstone can be determined as belonging to the given class when the matching score meets a predefined matching criterion (950). If the matching score does not meet the predefined matching criterion, it is determined that there is no match (960) between the given gemstone and the given class of gemstones. The predefined matching criterion can be a threshold determined based on, for example, experimental results and previous experience.

It is to be appreciated that in further embodiments the gemstone can be set in jewelry and thus part of its crown can be covered (e.g. by prongs). The above described technique can generate a unique identification of such gemstone in a similar manner as described with respect to FIGS. 5 and 7. By way of non-limiting example, the generated unique identification of a mounted gemstone can be further compared with previously generated unique identification of a loose gemstone in order to determine a match.

It is also noted that the identification process described with reference to FIG. 8 and FIG. 9 can be a part of identification process further comprising comparing the values of additional available parameters characterizing the gemstones to be compared (e.g. diameter, global image statistics such as average pixel level and contrast, etc.). Comparing additional parameters can be provided before and/or after the processes detailed therein.

It is to be understood that the invention is not limited in its application to the details set forth in the description contained herein or illustrated in the drawings. The invention is capable of other embodiments and of being practiced and carried out in various ways. Hence, it is to be understood that the phraseology and terminology employed herein are for the purpose of description and should not be regarded as limiting. As such, those skilled in the art will appreciate that the conception upon which this disclosure is based may readily be utilized as a basis for designing other structures, methods, and systems for carrying out the several purposes of the presently disclosed subject matter.

It will also be understood that the system according to the invention may be, at least partly, implemented on a suitably programmed computer. Likewise, the invention contemplates a computer program being readable by a computer for executing the method of the invention. The invention further contemplates a non-transitory computer-readable memory tangibly embodying a program of instructions executable by the computer for executing the method of the invention.

Those skilled in the art will readily appreciate that various modifications and changes can be applied to the embodiments of the invention as hereinbefore described without departing from its scope, defined in and by the appended claims.

The invention claimed is:

1. A computerized method of identifying a gemstone, the method comprising:
   obtaining by a computer a first unique identification associated with a first gemstone, the first unique identification corresponding to a first set of rotation-invariant values informative of rotational cross-correlation relationship characterizing a first representative group of one or more first images of the first gemstone, the one or more first images captured at one or more viewing angles relative to the first gemstone and to a first light pattern;
   obtaining by the computer a second unique identification associated with a second gemstone, the second unique identification corresponding to a second set of rotation-invariant values informative of rotational cross-correlation relationship characterizing a second representative group of one or more second images of the second gemstone, the one or more second images captured at one or more viewing angles relative to the second gemstone and to a second light pattern independently from capturing the one or more first images;
   calculating a matching score for said first and second unique identifications, the matching score being informative of a match between said first and second unique identifications; and
   identifying the first gemstone associated with the first unique identification and the second gemstone associated with the second unique identification as being the same gemstone when the matching score meets a predefined matching criterion;
   wherein obtaining the first unique identification comprises generating a first composite image corresponding to the images in the first representative group and calculating the first set of rotation-invariant values based on cross-correlation relationship between the first composite image and rotation versions thereof;
   wherein obtaining the second unique identification comprises generating a second composite image corresponding to the images in the second representative group and calculating the second set of rotation-invariant values based on cross-correlation relationship between the second composite image and rotation versions thereof; and
   wherein the first set is compatible with the second set;
   further comprising:
   dividing the first composite image into a plurality of first concentric areas and obtaining the first unique identification informative of all sets of rotation-invariant values generated, respectively for each first concentric area;
   dividing the second composite image into a plurality of second concentric areas corresponding to the first concentric areas and obtaining the second unique identification informative of all sets of rotation-invariant values generated, respectively for each second concentric area; and
   wherein calculating the matching score comprises separately calculating matching scores for each pair of a first concentric area and a corresponding second concentric area.

2. The method of claim 1, wherein the matching score is a normalized cross-correlation score.

3. The method of claim 1, wherein the first gemstone associated with the first unique identification and the second gemstone associated with the second unique identification are identified as being the same gemstone when matching scores of each pair meet respective predefined matching criterion.

4. The method of claim 1, wherein the concentric areas are concentric rings with equal square or equal radii.

5. The method of claim 1, wherein the one or more first images are captured by a first machine and the one or more second images are captured by a second machine other than the first machine, each machine calibrated with respect to the environment.

6. A computerized system comprising a processor configured to:
- obtain a first unique identification associated with a first gemstone, the first unique identification corresponding to a first set of rotation-invariant values informative of rotational cross-correlation relationship characterizing a first representative group of one or more first images of the first gemstone, the one or more first images captured at one or more viewing angles relative to the first gemstone and to a first light pattern;
- obtain a second unique identification associated with a second gemstone, the second unique identification corresponding to a second set of rotation-invariant values informative of rotational cross-correlation relationship characterizing a second representative group of one or more second images of the second gemstone, the one or more second images captured at one or more viewing angles relative to the second gemstone and to a second light pattern independently from capturing the one or more first images; and
- calculate a matching score for said first and second unique identifications, the matching score being informative of a match between said first and second unique identifications;
- wherein obtaining the first unique identification comprises generating a first composite image corresponding to the images in the first representative group and calculating the first set of rotation-invariant values based on cross-correlation relationship between the first composite image and rotation versions thereof;
- wherein obtaining the second unique identification comprises generating a second composite image corresponding to the images in the second representative group and calculating the second set of rotation-invariant values based on cross-correlation relationship between the second composite image and rotation versions thereof; and
- wherein the first set is compatible with the second set;
- wherein the processor is further configured to:
  - divide the first composite image into a plurality of first concentric areas and obtaining the first unique identification informative of all sets of rotation-invariant values generated, respectively for each first concentric area;
  - divide the second composite image into a plurality of second concentric areas corresponding to the first concentric areas and obtaining the second unique identification informative of all sets of rotation-invariant values generated, respectively for each second concentric area; and
  - wherein calculating the matching score comprises separately calculating matching scores for each pair of a first concentric area and a corresponding second concentric area.

7. The system of claim 6, wherein the processor is further configured to identify the first gemstone associated with the first unique identification and the second gemstone associated with the second unique identification as being the same gemstone when the matching score meets a predefined matching criterion.

8. The system of claim 6, wherein the second gemstone is a reference gemstone representing a given class of gemstones, and wherein the first gemstone is identified as belonging to the given class of gemstones when the first unique identification matches to the second unique identification.

9. The system of claim 6, wherein the processor is further configured to generate the first and/or the second unique identifications.

10. The system of claim 6, wherein the processor is further configured to receive the first and/or the second unique identifications from an external source configured to generate and/or to store the first and/or the second unique identifications.

11. The system of claim 6, wherein the first gemstone associated with the first unique identification and the second gemstone associated with the second unique identification are identified as being the same gemstone when matching scores of each pair meet respective predefined matching criterion.

* * * * *